United States Patent
Chenevier et al.

(10) Patent No.: US 8,663,682 B2
(45) Date of Patent: Mar. 4, 2014

(54) TASTE-MASKING COATED PARTICLES, PROCESS FOR THE PREPARATION THEREOF AND ORODISPERSIBLE TABLETS CONTAINING SAID COATED PARTICLES

(75) Inventors: Philippe Chenevier, Montreal (CA); Dominique Marechal, Laval (CA)

(73) Assignee: Ethypharm, Houdan (FR)

( * ) Notice: Subject to any disclaimer, the term of this patent is extended or adjusted under 35 U.S.C. 154(b) by 1865 days.

(21) Appl. No.: 10/544,071

(22) PCT Filed: Jan. 22, 2004

(86) PCT No.: PCT/EP2004/001754
§ 371 (c)(1),
(2), (4) Date: Jul. 28, 2005

(87) PCT Pub. No.: WO2004/066974
PCT Pub. Date: Aug. 12, 2004

(65) Prior Publication Data
US 2006/0062844 A1    Mar. 23, 2006

Related U.S. Application Data

(60) Provisional application No. 60/443,797, filed on Jan. 30, 2003.

(30) Foreign Application Priority Data

Feb. 3, 2003   (FR) ...................................... 03 01225

(51) Int. Cl.
*A61K 9/54* (2006.01)
*A61K 9/20* (2006.01)
*A61K 9/28* (2006.01)

(52) U.S. Cl.
USPC ........................... 424/458; 424/464; 424/474

(58) Field of Classification Search
USPC ......................................... 424/458, 464, 474
See application file for complete search history.

(56) References Cited

U.S. PATENT DOCUMENTS 5,098,715 A * 3/1992 McCabe et al. ............... 424/479
6,068,859 A * 5/2000 Curatolo et al. .............. 424/490

FOREIGN PATENT DOCUMENTS

| EP | 0 436 370 A1 | | 12/1990 | |
|---|---|---|---|---|
| EP | 1 279 402 A1 | | 7/2001 | |
| FR | 2 850 577 | * | 2/2003 | ............... A61K 9/20 |
| JP | 59 044311 A | | 9/1982 | |
| WO | WO 00/69420 A1 | | 5/2000 | |
| WO | WO 2004/066974 A1 | | 1/2004 | |

OTHER PUBLICATIONS

Junichi et al., English Translation of JP 590 44311, Mar. 12, 1984, pp. 1-18.*
Ishikawa et al., Preparation and evaluation of tablets rapidly disintegrating in saliva containing bitter-taste-masked granules by the compression method, Chem. Pharm. Bull. 47(10) 1451-1454 (1999).*
K. Canafe, et al., Die Pharmazie, "Studies on the formulation parameters and stabilities of micropellets comoprising acetytsalicyclic acid and ascorbic acid", vol. 48, No. 13, pp. 935-937, Dec. 1993.
Database WPI, AN 1984-098313, XP-002287685.
International Search Report, for PCT/EP2004/001754 mailed Jul. 26, 2004.

* cited by examiner

*Primary Examiner* — Aradhana Sasan
(74) *Attorney, Agent, or Firm* — Caesar, Rivise, Bernstein, Cohen & Pokotilow, Ltd.

(57) ABSTRACT

The present invention relates to a coated particle of active substance comprising a core, said core comprising the active substance and an acidic compound, said core being coated with a taste masking coating based on a polymer which is soluble at pH of 5 or less, and which is permeable at pH above 5.

25 Claims, No Drawings

TASTE-MASKING COATED PARTICLES, PROCESS FOR THE PREPARATION THEREOF AND ORODISPERSIBLE TABLETS CONTAINING SAID COATED PARTICLES

The present invention concerns taste-masking coated particles of active substance, oral formulations including said particles, particularly, orodispersible tablets, and a process for the preparation of said particles and said tablets.

In the context of the present invention, the term "orodispersible tablets" means tablets which are able to disintegrate in the buccal cavity in less than 60 seconds, preferably in less than 40 seconds, upon contact with saliva by formation of an easy-to-swallow suspension.

Many active substances which are intended for oral formulations present unpleasant, bitter or irritating taste. Such a taste must be masked in order to improve the palatability of the oral formulation and, consequently, the compliance with the treatment.

Taste-masking coating of such active substances is a well-known method used to solve said problem.

Specific polymers have been developed to comply with the taste-masking requirements. Said polymers present a solubility profile according to which they are insoluble at the saliva pH, i.e. pH=6-8 in order to prevent the active substance from contacting the tongue when the formulation is in the buccal cavity, but they are soluble at the stomach pH, i.e. pH=1-3, to allow the immediate release of the active substance and its absorption by the gastrointestinal mucous membrane.

The polymer is completely dissolved and the active substance is released when both following conditions are fulfilled:

the residence time of the coated particles in the stomach is sufficiently long, the pH of the stomach is sufficiently acid.

In some cases, both conditions are not fulfilled.

In fact, the residence time in the stomach can be very short. This is the case when the patient has eaten nothing and the stomach is empty. This is also the case when the patient drinks a large amount of water along with the drug, because the large amount of water causes the instinctive opening of the pyloric sphincter and the early emptying of the stomach contents into the duodenum.

In the case where the formulation consists in numerous particles presenting a size not greater than a few millimeters, the passage from the pylori to the duodenum (pH: 5.5-6.5) and the jejunum (pH 6-7) is very rapid.

Furthermore, the stomach pH can vary depending on whether the patient has eaten or not.

The uptake of an antacid can also modify the pH of the stomach which is then greatly increased and near neutral pH.

In such cases, the coated particles are in a medium where the polymer is no longer soluble, but only permeable. The release of the active substance depends then on the permeability of the film and on its thickness. The release of the active substance is then delayed.

In order to avoid or to minimize this difficulty, it has been proposed in the International Patent Application WO91/16043 to coat the active substance with a polymer membrane which is only soluble at pH above 5 and to add an acidic compound in order to prevent or to limit the dissolution of the polymer membrane in the buccal cavity.

However, the use of such a polymer membrane with an acidic compound is not suitable when the active substance must be immediately released since the polymers are enteric polymers which are insoluble at the stomach pH and are commonly used to protect active substances which can be damaged at stomach pH.

The solution proposed in WO91/16043, is thus not suitable for an immediate and complete release of active substances which need a taste-masking coating.

Up to now, no oral formulations comprising taste-masking particles which release the active substance at any pH value, i.e. at any level in the intestinal tract exist.

It is thus highly desirable to remedy this situation and to develop particles of active substance, which allow an immediate and complete release of the active substance even outside the stomach pH range and which present satisfactory taste-masking properties and which can thus be included into oral formulations, in particular, orodispersible tablet presenting a pleasant palatability.

The Applicant has now surprisingly found that these characteristics can be obtained by coated particles comprising a core, said core comprising the active substance and an acidic compound, said core being coated with a taste-masking coating based on a polymer which is soluble at pH of 5 or less, and which is permeable at pH above 5.

In the context of the present invention, the term "soluble polymer" refers to polymers which have the ability to dissolve in a determined pH, substantially independantly of the amount applied when coated onto active substance, and so as to release in one hour, at least 80% (w/w) of the active substance which would have been released without coating, in vivo or in vitro.

According to the present invention, at a pH above 5, the polymer is not soluble, but is permeable. At said pH, the acidic compound which is present in the core locally creates a very acidic micro-environment, which allows the quick dissolution of the polymer film and consequently the release of the active substance from the core.

The acidic compound which is comprised in the core of the particles according to the present invention, is a pharmaceutically acceptable organic acid which is selected from the group consisting of adipic acid, ascorbic acid, citric acid, fumaric acid, malic acid, succinic acid, tartaric acid, lactic acid, ascorbic acid or mixtures thereof.

According to an advantageous embodiment of the particles according to the invention, the amount of acidic compound ranges from 0.5 to 20% (w/w), preferably from 5 to 15% (w/w), and even more preferably from 5 to 10% (w/w) with respect to the total weight of the coated particles.

The core of the coated particles according to the invention comprises at least one active substance selected from the group comprising gastroenteric sedatives, antacids, antalgics, antiinflammatory agents, coronary vasodilatators, peripheral and cerebral vasodialators, anti-infectious agents, antibiotics, antivirals, antiparasitic agents, acaricids, anxiolytics, neuroleptics, stimulants of the central nervous system, antidepressants, antihistaminics, antidiarrhea agents, laxatifs, nutritional supplements, immunodepressants, hypocholesterolemiants, hormones, enzymes, antispasmodics, drugs which act on cardiac rythm, drugs used for treating arterial hypertension, antimigraine agents, anticoagulants, antiepileptics, myorelaxants, drugs used for treating diabetes, drugs used for treating thyroidal dysfunctions, diuretics, anorexigens, antiasthmatics, expectorants, anticoughing, mucoregulators, decongestionants, hypnotics, antinausea agents, hematopoietics, uricosurics, herb extracts, contrast agents or any other family of compounds, or mixtures thereof.

The invention is not suitable for active substances which are labile in acidic medium, such as in the stomach or in the microenvironment created by the acidic compound, and which need gastro-protection for oral administration, for example omeprazole, lansoprazole, or active substances which irritate the stomach mucus membrane, and which need sustained release because of their ulcerous effects, such as diclofenac, erythromycin and its derivatives and doxycycline.

The active substance which is initially in pulverulent or microcrystalline form, is used in the dry state for preparing particles, and in the form of organic or aqueous solution or suspension for layering on an inert carrier.

In the particles according to the invention, the core may further comprise at least one of the components selected from the group consisting of an inert carrier, a binder, a diluent agent or an antistatic agent and mixtures thereof.

The inert carrier may consist in any chemically and pharmaceutically inert excipient which exists in particular, crystalline or amorphous form. As examples, sugar derivatives such as lactose, sucrose, hydrolysed starch (maltodextrins), celluloses or mixtures thereof can be cited.

Mixtures of sucrose and starch or mixtures based on cellulose are also used as spherical inert carrier. The size of the inert carrier particles ranges between 50 and 500 μm, preferably between 90 and 150 μm.

The amount of binder can be up to 15% by weight, preferably up to 100% by weight with respect to the weight of the uncoated particles. Said binder is selected from the group comprising in particular cellulosic polymers, acrylic polymers, povidones, copovidones, polyvinylalcohols, alginic acid, sodium alginate, starch, pregelatinized starch, sucroses and their derivatives, guar gum, polyethyleneglycols, and mixtures thereof.

The amount of diluent agent can be up to 95%, preferably up to 50% by weight, with respect to the weight of the uncoated particles. Said diluent agent is selected from the group comprising cellulosic derivatives, preferably microcrystalline cellulose, polyols, preferably mannitol, starches, sugar derivatives such as lactose.

The amount of antistatic agent can be up to 10% by weight, preferably up to 3% by weight, with respect to the weight of the uncoated particles. Said antistatic agent is selected from the group comprising colloidal silica (Aerosil®), and preferably precipitated silica, in particular precipitated silica available undrer the trademark Syloïd® FP244, micronised or non micronised talc, and mixtures thereof.

According to the present invention, the core which comprises the active substance and the acidic compound is coated with a taste-masking coating based on a polymer which is soluble at a pH of 5 or less and which is permeable at a pH above 5.

According to an advantageous embodiment, said polymer is a methacrylic acid polymer or copolymer, preferably a copolymer of (butyl methacrylate-co-(2-dimethylaminoethyl)methacrylate-co-methyl methacrylate) 1:2:1, presenting an average weight of about 150,000, available from RÖHM under the trademark EUDRAGT® E100 or EUDRAGIT® EPO.

The thickness of the coating film depends on the solubility of the active substance at the saliva pH and of the degree of its unpleasant taste. In general, said thickness ranges from about 5 to 75 microns.

The amount of polymer ranges from 5 to 60%; preferably from 10 to 20% calculated as additional weight with respect to the weight of the core to be coated.

According to another embodiment, the coating further comprises at least one of the components selected from the group consisting of an antistatic agent, a plasticizer, surfactant, a lubricant, sweetener, color agent, flavors, and mixtures thereof.

The plasticizer is selected from the group consisting of triacetine, triethylcitrate, acetyltributyl citrate, tributyl citrate, diethylphthalate, polyethyleneglycols, polysorbates, mono-, diacetylated glycerides, or mixtures thereof. The plasticizer is used in proportions of at most about 40%, preferably between 15 and 30% by weight of the coating polymer.

The surfactant is selected from the group consisting of anionic, cationic, non ionic and amphoteric surfactants. The surfactant is used in proportions of at most about 20, preferably between 5 and 15 by weight of the coating polymer.

The antistatic agent is selected from the group consisting of micronised or non micronised talc, colloïdal silica (Aerosil 200), treated silica (Aerosil R972), precipitated silica (Syloïd FP244), and mixtures thereof. The antistatic agent is used in proportions of at most about 10%, preferably between 0 and 3%, and even more preferably, less than 1 % by weight of the coating polymer.

The lubricant is selected from the group consisting of magnesium stearate, stearic acid, sodium stearyl fumarate, micronised polyethyleneglycols, sodium benzoate, and mixtures thereof. The lubricant is used in proportions of at most about 10%, preferably between 0 and 3%, and even more preferably, less than 1 % by weight of the coating polymer.

Advantageously, the particle size of the coated particles ranges between 100 and 800 μm and preferably between 200 and 500 μm.

The particle sizes are measured according to conventional methods such as by sieving or by laser diffraction.

The invention also concerns a process for preparing the above-described coated granules.

The process comprises the steps consisting in:
preparing particles containing the active substance, and the acidic compound, and optionally at least one excipient selected from the group consisting in an inert carrier, a binder, an antistatic agent, a diluent agent, a permeabilizing agent and mixtures thereof,
coating the particles by spraying thereon a coating composition based on a polymer which is soluble at a pH of 5 or less and which is permeable at a pH above 5,
drying the thus obtained coated granules.

In this process the mixing, granulating and coating steps can be performed in different apparatuses or in the same apparatus, each step being performed in the presence of a mixture of excipients which may be identical or different.

In an advantageous embodiment, each step is performed on a fluidized air-bed, such as for example, but not limited to Glatt GPCG-1, GPCG-5 or GPCG 120.

According to an advantageous embodiment, the polymer used for granulating and the polymer used for coating are identical. The granulation step differs from the coating step by the operational parameters such as spraying flow, atomization pressure of the mixture of excipients.

Advantageously, from 10 to 30% of the mixture of excipients are sprayed during the granulation step, the complement to 100% being sprayed during the coating step.

For granulating, bottom spray granulation, tangential spray granulation, top spray granulation or high shear granulation can be used, bottom spray granulation being preferred.

For coating, bottom, top and tangential spray methods can be used as well as layering method, the bottom spray method of coating being preferred.

According to a first embodiment, the preparation of the particles, comprises the following steps:
dry mixing active substance under pulverulent form or under crystalline form, with the acidic compound and optionally with a diluent agent and an antistatic agent, granulating the thus obtained mixture with a binder used under dry or wet form depending on the granulation type, drying.

When a fluidized air apparatus is used, a pulverulent mixture of active substance, and optionally the diluent agent and the antistatic agent is charged into the apparatus, then a solution or a suspension of excipients comprising at least a binder is sprayed thereon.

According to a second embodiment, the preparation of the particles consists in the following steps:

spraying onto an inert carrier a solution or dispersion containing the active substance and the acidic compound, both being sprayed simultaneously or subsequently, drying.

According to a third embodiment, the preparation of the particles comprises the following steps:

providing active substance particles, spraying thereon a solution of the acidic-compound, drying.

The particles obtained according to the above-described processes are then coated by spraying thereon a coating composition containing the polymer in solution, dispersion, colloidal dispersion or suspension in a solvent selected from the group consisting in water, organic alcohols such as ethanol, isopropanol, acetone, and mixtures thereof, and then drying.

Preferably the different steps are performed on a fluidized air apparatus, wherein both the position and the orientation of the spraying outlet of said apparatus can be selected.

This selection results in the possibility to check the growth rate of the particles and to avoid the binding phenomena due to the nature of the active substance, binding or coating composition, and the different parameters of the process.

The coated particles according to the invention can be used in any oral formulations, and are particularly suitable for formulations in which the coated particles are in contact with saliva.

Another object of the invention is an oral formulation containing said coated particles.

Said oral formulation can be a pharmaceutical powder packaged in a unidose bag, or drinkable suspensions which are presented in liquid form or as extemporaneous preparations to which water needs to be added before use, or tablets which are orodispersible or dispersible in a small amount of water.

According to an advantageous embodiment, the oral formulation according to the invention is an orodispersible tablet intended to disintegrate or to dissolve in the buccal cavity upon contact with saliva in less than 60 seconds, preferably in less than 40 seconds, by formation of an easy-to-swallow suspension of coated particles.

The disintegration time corresponds to the time between the moment when the tablet is placed in the buccal cavity in contact with saliva and the moment when the suspension resulting from the disintegration without chewing of the tablet is swallowed.

Oral disintegrable multiparticulate tablets have for example, already been described in EP 548356, EP 636364, EP1003484, EP 1058538, WO 98/46215, WO 00/06126, WO 00/27357 and WO00/51568, the contents of which are hereby incorporated by reference. The active ingredient is in the form of coated microcrystals or coated microgranules.

The coated particles are released in the buccal cavity when the tablet disintegrates or dissolves in the presence of saliva. Then, they are swallowed and they release the active substance where they are in the gastro-enteric tract (stomach, duodenum), i.e., independently of the surrounding pH.

The orodispersible tablets according to the present invention contain the above described coated granules, and a mixture of excipients comprising at least one disintegrating agent, a soluble diluent agent, a lubricant and optionally a swelling agent, a permeabilising agent, an antistatic agent, sweeteners, flavoring agents and colorants.

According to an advantageous embodiment of the orodispersible tablets, the ratio of the mixture of excipients to the coated granules is 0.4 to 10, preferably 1 to 5 parts by weight.

The disintegrating agents are selected from the group consisting of croscarmellose, crospovidone and mixtures thereof.

The proportion of disintegrating agents being 1 to 20% by weight, preferably 5 to 1 5% by weight, in the case of a mixture, each disintegrating agent being comprised between 0.5 and 15% by weight, preferably 5 to 10 % by weight, and the proportion of soluble agent being 20 to 90% by weight, preferably 30 to 50% by weight, based in each case on the weight of the tablet.

The diluent agent is selected from the group comprising in particular lactose, cellulosic derivatives, preferably microcrystalline cellulose, and soluble agents with binding properties, preferably polyols having less than 13 carbon atoms.

The polyol having less than 13 carbon atoms, is preferably selected from the group consisting in mannitol, xylitol, sorbitol and maltitol.

The diluent agent is in the form of a directly compressible product with an average particle size of 100 to 500 µm, or in the form of a powder with an average particle size of less than 100 µm, the powder being used alone or in admixture with the directly compressible product.

According to a preferred embodiment, the polyol is used in the form of a directly compressible product.

In a second preferred embodiment, a mixture of a directly compressible polyol and a polyol in powder form is used. In this case the polyols can be identical or different, the ratio of directly compressible polyol to powder polyol being from 99/1 to 20/80, preferably from 80/20 to 20/80.

The lubricant is selected from the group consisting of magnesium stearate, stearic acid, sodium stearyl fumarate, micronised polyoxyethyleneglycols, sodium benzoate and mixtures thereof.

The amount of lubricant is from 0.02 to 2 percent, preferably from 0.5 to 1 percent (weight of the lubricant/total weight of the tablet).

The lubricant can be dispersed within the mixture of excipients, or according to an advantageous embodiment, it can be dispersed on the surface of the tablet.

The swelling agent is selected from the group consisting of microcrystalline cellulose, starches, modified starches, and mixtures thereof.

The proportion of swelling agent is between 1.0 and 15% by weight, based on the weight of the tablet.

The antistatic agent is selected from the group consisting of colloidal silica, precipitated silica, micronised or non-micronised talc, and mixtures thereof. The proportion of antistatic agent is between 0.5% and 5% by weight with respect to the weight of the tablet.

The permeabilizing agent used is a compound selected from the group comprising silicas with a high affinity for aqueous solvents, such as precipitated silica, better known by the trademark Syloïd®, maltodextrins, β-cyclodextrins and mixtures thereof.

The permeabilizing agent allows the creation of a hydrophilic network which facilitates the penetration of saliva and hence assists the disintegration of the tablet.

The proportion of permeabilising agent is between 0.5 and 5% by weight, based on the weight of the tablet.

A sweetener and optionally a flavoring and a colorant are also included in the mixture of excipients forming part of the composition of the tablets according to the invention.

The sweetener can be selected from the group comprising aspartame, potassium acesulfame, sodium saccharinate, neohesperidin dihydrochalcone, sucralose, monoammonium glycyrrhizinate, and mixtures thereof.

The flavorings and colorants are those conventionally used in the pharmaceutical filed for the preparation of tablets.

According to an advantageous embodiment, the mixture of excipients comprises:
from 1 to 25%, preferably from 5 to 10% by weight of disintegrating and/or swelling agent;
from 30 to 90%, preferably from 40 to 70% by weight of diluent agent;
from 0.02 to 2%, preferably from 0.5 to 1 % by weight of lubricant,
from 0.5 to 5%, by weight of permeabilising agent,
the percentages being calculated with respect to the weight of the tablet.

The invention also concerns the process for preparing orodispersible tablets, comprising the coated particles.

The process according to the invention comprises the following steps consisting in:
dry mixing the coated particles obtained according to the above described process with a mixture of excipients comprising at least one disintegrating agent, a soluble diluent agent, a lubricant and optionally a swelling agent, a permeabilising agent, sweeteners, flavoring agents and colorants;
tabletting the mixture to obtain a tablet.

The tabletting step can be performed on a alternate or rotative press.

The strength used during the tabletting step ranges from 5 kN to 50 kN, preferably from 5 kN to 15 kN.

The hardness of the orodispersible tablets ranges from 1 to 10 kp, preferably from 1 to 5 kp, such as measured according to the method described in the European Pharmacopeia (2.9.8), 1 kp being 9.8N.

The hardness of the tablets is such that:
the tablets present a friability as measured according to the European Pharmacopeia of less than 2%,
the dissolution profile of the tablets is identical to the dissolution profile of the coated particles contained therein; and
the disintegration time of orodispersible tablets in the buccal cavity is 60 seconds or less, preferably, 40 seconds or less.

The tablets may have a diameter of 6 to 17 mm. They can be round, oval, oblong; they may have present an outer surface which is flat or concave, and optionally they may be marked.

In the case of orodispersible tablets, poleopunches can adventageously be used.

Depending on the dosage, the tablets have a weight of 0.1 to 2.0 grams.

The invention is illustrated in further detail in the following examples. These examples are only illustrative and not limitative.

EXAMPLES

In the examples below, the following products are used:
HPMC: hydroxypropylméthylcellulose sold by SHIN-ETSU under the trademark Pharmacoat® 603;
mannitol: Pearlitol® 200SD sold by ROQUETTE;
Microcrystalline cellulose: Avicel®PH102 sold by FMC;
Colloidal silica: Syloïd®244FP sold by BASF;
Methacrylate copolymer: Eudragit® E100 sold by Röhm;
Sucralose: sold by SPLENDA.

Example 1

Coated Particles of Fexofenadine HCl

In a fluidized bed GPCGI GLATT, with a Wurster buse (bottom spray), a hydroalcoholic solution containing 1000 g of fexofenadine HCl, 300 g of HPMC as binder (30% by weight with respect to fexofenadine) and 100 g of citric acid (10% by weight with respect to fexofenadine) was sprayed onto 100 grammes of sucrose crystals with a size between 80 and 150 μm.

2400 g of the cores obtained in the preceding step are coated in a fluidized bed GPCG3 GLATT equipped with a Wurster buse, by spraying thereon an alcoholic solution of Eudragt®E100 comprising 10% by weight with respect to the weight of dry polymer, of colloidal silica.

The amount of Eudragit®E100 was 30% calculated as additional weight with respect to the weight of the cores.

The final formula of the coated particles is given in Table 1 below:

TABLE 1

| Components | % (w/w) |
| --- | --- |
| Fexofenadine HCl | 37.2 |
| HPMC | 11.1 |
| Citric Acid | 3.8 |
| Sucrose crystals | 23.1 |
| Eudragit ® E100 | 22.5 |
| Colloidal Silica | 2.3 |
| Isopropylic alcohol | n/a |
| Purified water USP | n/a |
| TOTAL | 100 |

Example 2

Orodispersible Tablets of Fexofenadine HCl 30 mg

The particles obtained in example 1 are mixed with excipients, according to table 2. The mixture thus obtained is then tabletted with a SVIAC PR6 press equipped with 6 round punches of 12 mm diameter to obtain a unit dose of about 30 mg.

TABLE 2

| | % (w/w) | mg/tablet |
| --- | --- | --- |
| Coated particles of fexofenadine HCl | 22.5 | 90.0 |
| Mannitol | 54.3 | 217.2 |
| Crospovidone CL | 10.0 | 40.0 |
| Microcrystalline cellulose | 10.0 | 40.0 |
| Sucralose ® | 1.5 | 6.0 |
| Strawberry flavour | 0.7 | 2.8 |
| colloïdal Silica | 0.5 | 2.0 |
| magnesium Stearate | 0.5 | 2.0 |
| TOTAL | 100 | 400 |

The tablets present the characteristics mentioned in Table 3 below:

TABLE 3

| | |
|---|---|
| Weight (mg) | 400 |
| hardness (kP) | 3.5 |
| Friability (%) | 0.6 |
| Buccal Disintegration (s) | 20 |

Example 3

Orodispersible Tablets of Fexofenadine HCl 180 mg

The particles obtained in example 1 are mixed with excipients, according to table 4. The mixture thus obtained is then tabletted with a SVIAC PR6 press equipped with 6 round punches of 16 mm diameter, to obtain a unit dose of about 180 mg.

TABLE 4

| | % (w/w) | mg/tablet |
|---|---|---|
| Coated particles of fexofenadine HCl | 42.5 | 542.3 |
| Mannitol | 33.8 | 431.3 |
| Crospovidone CL | 10.0 | 127.6 |
| Microcrystalline cellulose | 10.0 | 127.6 |
| Sucralose ® | 1.5 | 19.1 |
| Mint flavour | 1.2 | 15.3 |
| colloïal Silica | 0.5 | 6.4 |
| magnesium Stearate | 0.5 | 6.4 |
| TOTAL | 100 | 1276 |

The tablets present the characteristics mentioned in Table 5 below:

TABLE 5

| | |
|---|---|
| Weight (mg) | 1276 |
| hardness (kP) | 3.5 |
| Friability (%) | 1.4 |
| Buccal Disintegration (s) | 30 |

Example 4

Comparative Example

Coated particles are prepared according to example 1, without addition of citric acid.

The formula of coated particles is given in Table 6 below:

TABLE 6

| Components | % (w/w) |
|---|---|
| Fexofenadine HCl | 42.0 |
| HPMC | 2.0 |
| Sucrose crystals | 42.0 |
| Eudragit ® E100 | 12.9 |
| Colloïdal Silica | 1.1 |
| Isopropylic alcohol | n/a |
| Purified water USP | n/a |
| TOTAL | 100 |

Orodispersible tablets according to example 3 above are then prepared.

The composition of the orodispersible tablets is given in Table 7 below.

TABLE 7

| | % (w/w) | mg/tablet |
|---|---|---|
| Coated particles of fexofenadine HCl | 35 | 430.0 |
| Mannitol | 41.9 | 515.8 |
| Crospovidone CL | 10.0 | 123.1 |
| Microcrystalline cellulose | 10.0 | 123.1 |
| Sucralose ® | 1.5 | 18.5 |
| Raspberry flavour | 0.7 | 7.4 |
| Colloïdal Silica | 0.5 | 6.2 |
| Magnesium Stearate | 0.5 | 6.2 |
| TOTAL | 100 | 1231 |

The tablets present the characteristics mentioned in Table 8 below:

TABLE 8

| | |
|---|---|
| Weight (mg) | 1231 |
| hardness (kP) | 5.5 |
| Friability (%) | 0.1 |
| Buccal Disintegration (s) | 28 |

Example 5

Comparative Dissolution Profiles at pH 3 and pH 6.8:

A dissolution profile is made with the orodispersible tablets of example 3 and example 4, at pH=3 and at pH=6.8.
The conditions of dissolution are the following:
Apparatus: USP type II
Rate of rotation: 100 rpm
Volume: 900 ml
Temperature: 37.0° C.±0.5° C.
Detection: Direct UV spectrophotmetry at 220 nm
Dissolution medium:
  at pH=3: HCl 0.001N
  at pH=6.8: phosphate buffer pH=6.8
The results are given in tables 9 and 10 below:

TABLE 9

| Medium pH 3 | Released Fexofenadine % (w/w) | |
|---|---|---|
| Time (minutes) | Example 3 | Example 4 |
| 2.5 | 49 | 51 |
| 15 | 100 | 100 |
| 30 | 100 | 100 |
| 60 | 100 | 100 |

TABLE 10

| Medium pH 6,8 | Released fexofenadine % (w/w) | |
|---|---|---|
| Time (minutes) | Example 3 | Example 4 |
| 2.5 | 28 | 6 |
| 15 | 73 | 29 |
| 30 | 91 | 36 |
| 60 | 98 | 52 |

In a medium which presents a pH equivalent to the stomach pH, the organic acid has no influence on the release of the fexofenadine. At pH=6.8, the presence of the organic acid in the core of the coated particles helps the solubilization of the coating film and allows the release of the fexofenadine equivalent to the release of fexofenadine in the medium presenting the stomach pH., while the release of the fexofenadine of the comparative example (with no organic acid in the core) is delayed.

The invention claimed is:

1. A coated particle of active substance comprising a core, said core comprising the active substance and an acidic compound, said core being coated with a taste masking coating comprising a film-forming polymer which is soluble at pH of 5 or less, and which is permeable at pH above 5, wherein the coating is devoid of any other film-forming polymer and the coated particle is adapted for an immediate and complete release of the active substance independently of a surrounding pH, such that: (a) when the surrounding pH is 5 or less, the taste masking coating is adapted to dissolve and release the active substance; and (b) when the surrounding pH is above 5, the acidic compound is adapted to dissolve the taste masking coating and release the active substance.

2. The coated particle according to claim 1, wherein the acidic compound is a pharmaceutically acceptable organic acid.

3. The coated particle according to claim 2, wherein the organic acid is a member selected from the group consisting of adipic acid, ascorbic acid, citric acid, fumaric acid, malic acid, succinic acid, tartaric acid, lactic acid and mixtures thereof.

4. The coated particle of claim 1, wherein an amount of the acidic compound ranges from 0.5 to 20% (w/w) with respect to a total weight of the coated particles.

5. The coated particle of claim 4, wherein the amount of acidic compound ranges from 5 to 15% (w/w) with respect to the total weight of the coated particles.

6. The coated particle of claim 5, wherein the amount of acidic compound ranges from 5 to 10% (w/w) with respect to the total weight of the coated particles.

7. The coated particle of claim 1, wherein the core further comprises at least one member selected from the group consisting of an inert carrier, a binder, a diluent agent or an antistatic agent and mixtures thereof.

8. The coated particle of claim 1, wherein the coating further comprises at least one member selected from the group consisting of an antistatic agent, a plasticizer, a surfactant, a lubricant, sweeteners, colorants, flavors, and mixtures thereof.

9. A process for preparing coated particles according to claim 1, comprising the steps consisting of:
preparing particles containing the active substance, and the acidic compound, and optionally at least one excipient selected from the group consisting in an inert carrier, a binder, an antistatic agent, a diluent agent, a permeabilizing agent and mixtures thereof,
coating the particles by spraying thereon a coating composition based on a polymer which is soluble at a pH of 5 or less and which is permeable at a pH above 5,
drying the thus obtained coated granules.

10. Orodispersible tablets comprising a plurality of the coated particle of claim 1, and a mixture of excipients comprising at least one disintegrating agent, a soluble diluent agent, a lubricant and optionally a swelling agent, a permeabilizing agent, an antistatic agent, sweeteners, flavorings and colorants.

11. The orodispersible tablets according to claim 10, in which a ratio of the mixture of excipients to coated particles is 0.4 to 10, the mixture of excipients comprising:
at least one disintegrating agent,
a soluble diluent agent which presents binding properties,
a lubricant,
a permeabilizing agent, and optional sweeteners, flavorings and colorants.

12. The orodispersible tablets according to claim 10, in which the disintegrating agent is a member selected from the group consisting of croscarmellose, crospovidone and mixtures thereof.

13. The orodispersible tablets according to claim 10 in which the soluble diluent agent with binding properties consists of a polyol having less than 13 carbon atoms and being either in a form of a directly compressible product with an average particle size of 100 to 500μm, or in a form of a powder with an average particle size of less than 100μm.

14. The orodispersible tablets according to claim 10, in which the permeabilizing agent is a silica with a high affinity for aqueous solvents.

15. The orodispersible tablets according to claim 10, in which the lubricant is a member selected from the group consisting of magnesium stearate, stearic acid, sodium stearyl fumarate, micronised polyoxyethyleneglycols (micronised Macrogol 6000), sodium benzoate and mixtures thereof.

16. The orodispersible tablets according to claim 10, in which a proportion of disintegrating agent is 1 to 20% by weight and a proportion of soluble agent is 20 to 90% by weight based in each case on a weight of the tablet.

17. Process for preparing orodispersible tablets according to any one of claims 10 to 16, which comprises the steps of:
dry mixing the coated particles obtained according to the above described process with a mixture of excipients comprising at least one disintegrating agent, a soluble diluent agent, a lubricant and optionally a swelling agent, a permeabilising agent, sweeteners, flavoring agents and colorants;
tabletting the mixture to obtain a tablet.

18. The orodispersible tablets according to claim 11, wherein the ratio of the mixture of excipients to the coated granules is 1 to 5 parts by weight.

19. The orodispersible tablets according to claim 13, wherein the polyol is a member selected from the group consisting of mannitol, xylitol, sorbitol and maltitol, provided that: (a) sorbitol cannot be used alone; (b) when there is only one soluble diluent agent with binding properties, the one soluble diluent agent is in a directly compressible form;
(c) when there are at least two soluble diluent agents with binding properties, at least one is in a directly compressible form and at least one other is in a powder form, wherein the polyols can be the same or different and a ratio of directly compressible polyol to powder polyol is 99/1 to 20/80.

20. The orodispersible tablets according to claim 19, wherein the ratio of directly compressible polyol to powder polyol is 80/20 to 20/80.

21. The orodispersible tablets according to claim 14, wherein said silicas with a high affinity for aqueous solvents are members selected from the group consisting of precipitated silica, maltodextrins, β-cyclodextrins and mixtures thereof.

22. The orodispersible tablets according to claim 16, wherein the proportion of disintegrating agent is 5 to 15% by weight and the proportion of soluble agent is 30 to 50% by weight, based in each case on the weight of the tablet.

23. A coated particle of active substance comprising a core, said core comprising the active substance and an acidic compound, said core being coated with a taste masking coating consisting of a polymer which is soluble at pH of 5 or less, and which is permeable at pH above 5, and at least one member selected from the group consisting of an antistatic agent, a plasticizer, a surfactant, a lubricant, sweeteners, colorants, flavors, and mixtures thereof, wherein the coated particle is adapted for an immediate and complete release of the active substance independently of a surrounding pH, such that: (a) when the surrounding pH is 5 or less, the taste masking coating is adapted to dissolve and release the active substance; and (b) when the surrounding pH is above 5, the acidic compound is adapted to dissolve the taste masking coating and release the active substance.

24. A method for releasing an active substance into the gastro-enteric tract of a patient independently of the surrounding pH, said method comprising orally administering to the patient a coated particle according to claim 1, wherein the taste masking coating is dissolved by at least one of: (i) surrounding fluids having a pH of 5 or less and (ii) the acidic compound, such that the active substance is released independently of the surrounding pH.

25. The method according to claim 24, wherein the surrounding fluids have a pH greater than 5, and the taste masking coating is dissolved by the acidic compound.

* * * * *